United States Patent
Kim (10) Patent No.: US 10,335,106 B2
(45) Date of Patent: Jul. 2, 2019

(54) COMPUTING SYSTEM AND METHOD FOR IDENTIFYING AND VISUALIZING CEREBRAL THROMBOSIS BASED ON MEDICAL IMAGES

(71) Applicant: Infinitt Healthcare Co., Ltd., Seoul (KR)

(72) Inventor: Han Young Kim, Seoul (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 140 days.

(21) Appl. No.: 15/719,656

(22) Filed: Sep. 29, 2017

(65) Prior Publication Data

US 2019/0099145 A1 Apr. 4, 2019

(51) Int. Cl.
*A61B 6/00* (2006.01)
*A61B 5/02* (2006.01)
*A61B 5/00* (2006.01)

(52) U.S. Cl.
CPC .......... *A61B 6/504* (2013.01); *A61B 5/02007* (2013.01); *A61B 6/507* (2013.01); *A61B 5/0062* (2013.01); *A61B 6/463* (2013.01)

(58) Field of Classification Search
CPC combination set(s) only.
See application file for complete search history.

(56) References Cited

U.S. PATENT DOCUMENTS

| | | | |
|---|---|---|---|
| 7,165,010 B2* | 1/2007 | Mancini | A61B 5/02007 702/182 |
| 8,019,142 B2 | 9/2011 | Nowinski et al. | |
| 8,170,304 B2 | 5/2012 | Tek et al. | |
| 8,366,627 B2 | 2/2013 | Kashif et al. | |
| 8,594,950 B2* | 11/2013 | Taylor | A61B 5/02007 702/19 |
| 8,821,402 B2 | 9/2014 | Kashif et al. | |
| 9,501,620 B2* | 11/2016 | Okell | A61B 6/507 |
| 2003/0171894 A1* | 9/2003 | Giovanni Battista Mancini | A61B 5/02007 702/182 |
| 2007/0263915 A1* | 11/2007 | Mashiach | G06K 9/342 382/130 |
| 2010/0278405 A1* | 11/2010 | Kakadiaris | G16H 50/30 382/131 |

(Continued)

*Primary Examiner* — Anand P Bhatnagar (74) *Attorney, Agent, or Firm* — Mintz Levin Cohn Ferris Glovsky and Popeo, P.C.; Kongsik Kim (57) ABSTRACT

Disclosed are a computing system and method for identifying and visualizing a thrombosis. The method includes: registering an acquired computer tomography (CT) image of an examinee and a computer tomography angiography (CTA) image-based average standard model to each other; identifying a candidate blood vessel region from the CT image based on the results of the registration; acquiring a volume, selected by applying a threshold value for the brightness of the CT image to the candidate blood vessel region, as a first thrombosis candidate region; acquiring at least part of the first thrombosis candidate region as a second thrombosis candidate region based on the size information of the first thrombosis candidate region; and visualizing the second thrombosis candidate region by assigning a visual effect, adapted to distinguish the second thrombosis candidate region from the remaining portion of the CT image, to the second thrombosis candidate region.

16 Claims, 8 Drawing Sheets

(56) References Cited

U.S. PATENT DOCUMENTS

| | | | |
|---|---|---|---|
| 2011/0257505 A1* | 10/2011 | Suri | A61B 6/504 |
| | | | 600/408 |
| 2011/0257545 A1* | 10/2011 | Suri | A61B 5/02007 |
| | | | 600/508 |
| 2014/0357965 A1 | 12/2014 | Kashif et al. | |
| 2016/0224744 A1 | 8/2016 | Grady et al. | |
| 2017/0018081 A1 | 1/2017 | Taylor et al. | |
| 2017/0128036 A1 | 5/2017 | Tanter et al. | |
| 2017/0337343 A1* | 11/2017 | Kakadiaris | G06F 19/00 |
| 2018/0008152 A1* | 1/2018 | Watanabe | A61B 5/0285 |
| 2018/0174490 A1* | 6/2018 | Randles | G06T 7/0014 |

* cited by examiner

COMPUTING SYSTEM AND METHOD FOR IDENTIFYING AND VISUALIZING CEREBRAL THROMBOSIS BASED ON MEDICAL IMAGES

TECHNICAL FIELD

The present invention relates generally to a method of processing and visualizing medical images, and more specifically to a computing system and method for identifying and visualizing a candidate region for a cerebral thrombosis based on medical images.

BACKGROUND ART

A stroke is caused by the abrupt loss of a nerve function attributable to the interruption of cerebral perfusion resulting from the occlusion or rupture of a blood vessel, is a principal cause of physical disabilities and deaths, and has a serious influence on the health of the elderly persons and middle-aged persons. Strokes are basically classified into a cerebral infarction and a cerebral hemorrhage. In particular, a cerebral infarction has been experienced by about 80% of the total stroke patients, and is known as a significantly serious disease that threatens the survival of humans.

When rapid diagnosis and treatment are not performed in the early stage of the occurrence of a lesion, a stroke is accompanied by serious aftereffects, such as hemiplegia, sensation, language and vision disorders, dementia, etc. In order to minimize such secondary damage, it is extremely important to detect the occlusion or rupture of a blood vessel in its early stage.

Computer tomography (CT) and magnetic resonance imaging (MRI) are used to diagnose a stroke. Meanwhile, magnetic resonance angiography (MRA), computed tomography angiography (CTA), etc. using a contrast agent are used to focus on a cerebral blood vessel where a stroke occurs.

Functional MRI (f-MRI) is used to acquire functional images of a cerebral blood vessel and a cerebral region. A cerebral image analysis technique using f-MRI is disclosed in U.S. Patent Application Publication No. US 2017/0128036 entitled "Method and Device for Functional Imaging of the Brain." This prior art proposes a method of extracting a functional cerebral region from a cerebral image by using a cerebral vascular atlas.

A medical image processing technology for analyzing a cerebral blood flow disorder is disclosed in U.S. Patent Application Publication No. US 2016/0224744 entitled "Systems and Methods for Embolism Prediction using Embolus Source and Destination Probabilities." This prior art proposes a model which calculates pressure applied to a narrowed cerebral blood vessel by applying fluid mechanics to the cerebral blood vessel and then predicts the possibility of a blood flow disorder.

Another cause for a stroke or cerebral infarction is the occlusion of a blood vessel which is caused by a cerebral thrombosis. A cerebral thrombosis is a cause for cerebral arteriosclerosis, etc., and refers to a phenomenon in which thrombi are accumulated in a stenosed portion of a cerebral blood vessel and occlude the cerebral blood vessel. A cerebral thrombosis is distinctive from a cerebral embolism in which thrombi generated in another organ, such as the valves of the heart, or the like, move to a cerebral blood vessel along with a blood flow and occlude the cerebral blood vessel. In CT and MRI images, etc., it is difficult to distinguish a cerebral thrombosis from adjacent tissues.

Meanwhile, although a blood vessel region can be emphasized in CTA and MRA images, a problem remains still in that the emphasis does not directly help to search for the location of a thrombosis.

In other words, the conventional technologies including f-MRI, CT, MRI, CTA, MRA, etc. have their limitations on searching for the location of a cerebral thrombosis. CTA imaging has its limitations in terms of the range of application due to an increase in the exposure of a patient to radioactive rays, the side effect of a contrast agent, etc.

SUMMARY OF THE DISCLOSURE

The present invention has been conceived to overcome the above-described problems of the prior art, and an object of the present invention is to provide technology which enables a candidate region where there is possibility that a thrombosis is present to be selected even from a general CT image, and which can reduce a target region in which a thrombosis is searched for, thereby enabling an examiner to easily and accurately search for and analyze a thrombosis.

An object of the present invention is to provide technology which can resolve a problem in which it is difficult to search for a thrombosis because a contrast between a thrombosis and adjacent tissues is not obvious in a CT image, and which enables a thrombosis to be accurately searched for by using a specific threshold value (ranging from 40 to 100 HU) for a thrombosis and rapidly excluding a region, other than a cerebral blood vessel, from a search target range.

An object of the present invention is to provide technology which can increase the accuracy of a search for a thrombosis in selective conjunction with a contrast-enhanced CTA image. An object of the present invention is to provide technology which can generate an average standard model by segmenting only important cerebral blood vessel regions from a plurality of CTA images, and, thus, can propose an average standard model which can function as a mask layer required for the selection of a candidate region where there is possibility that an actual blood vessel is present and can also propose a method of utilizing the average standard model.

Another object of the present invention is to provide technology which can further increase the accuracy of a search for a thrombosis when both CT and CTA images of the same patient are simultaneously utilized.

In accordance with an aspect of the present invention, there is provided a method of identifying and visualizing a thrombosis which is performed by a processor of a computing system, the method including: registering an acquired computer tomography (CT) image of an examinee(without contrast agent) and a computer tomography angiography (CTA) image-based average standard model to each other; identifying a candidate blood vessel region from the first medical image of the examinee based on the results of the registration to the average standard model; acquiring a volume, selected by applying a threshold value for the brightness of the first medical image to the candidate blood vessel region, as a first thrombosis candidate region; acquiring at least part of the first thrombosis candidate region as a second thrombosis candidate region based on the size information of the first thrombosis candidate region; and visualizing the second thrombosis candidate region by assigning a visual effect, adapted to distinguish the second thrombosis candidate region from the remaining portion of the first medical image of the examinee, to the second thrombosis candidate region.

The identifying may include: discriminating a first region where blood vessels are distributed from the first medical image of the examinee based on the results of the registration to the average standard model; and setting at least part of the discriminated first region as the candidate blood vessel region.

The method may further include: displaying a second medical image, i.e., an acquired CTA image of the examinee, in parallel with the first medical image; registering the second medical image and the first medical image to each other; changing the display of the first medical image in response to an user input for the first medical image; and changing the display of the second medical image in response to the changed display of the first medical image.

The method may further include: detecting a thrombosis-occluded region where a blood vessel is disconnected or at least a part of the blood vessel is absent in the second medical image registered to the first medical image; and detecting a region of the detected thrombosis-occluded region matching the second thrombosis candidate region as a thrombosis location region.

The method may further include: receiving the first sample image of another CTA image; segmenting a first cerebral blood vessel region from the first sample image; setting the first center line of the segmented first cerebral blood vessel region, and measuring the first diameter of the first cerebral blood vessel region; and generating the CTA image-based average standard model by using information about the first boundary of the segmented first cerebral blood vessel region, information about the first center line of the first cerebral blood vessel region, and information about the first diameter of the first cerebral blood vessel region.

The method may further include: receiving a second sample image of another CTA image; segmenting a second cerebral blood vessel region from the second sample image; setting the second center line of the segmented second cerebral blood vessel region, and measuring the second diameter of the second cerebral blood vessel region; and updating the CTA image-based average standard model based on information about the second boundary of the segmented second cerebral blood vessel region, information about the second center line of the second cerebral blood vessel region, and information about the second diameter of the second cerebral blood vessel region.

In accordance with another aspect of the present invention, there is provided a method of identifying and visualizing a thrombosis which is performed by a processor of a computing system, the method including: identifying a blood vessel region from a second medical image, i.e., an acquired computer tomography angiography (CTA) image of an examinee; registering the identified blood vessel region and a CTA image-based average standard model to each other; detecting a thrombosis-occluded region based on a difference between the identified blood vessel region and the registered average standard model; and visualizing the detected thrombosis-occluded region by assigning a visual effect, adapted to distinguish the detected thrombosis-occluded region from the remaining portion of the second medical image of the examinee, to the detected thrombosis-occluded region.

The detecting may include identifying a region of the identified blood vessel region, where a blood vessel is disconnected or at least a part of the blood vessel is absent, as the thrombosis-occluded region by comparing the identified blood vessel region with the average standard model.

The method may further include: receiving a first medical image (CT image) including the anatomical structure information of the examinee; registering the first medical image and the second medical image to each other; and visualizing the thrombosis-occluded region, detected from the second medical image (CTA image), in the first medical image registered to the second medical image.

The method may further include: displaying a first medical image, including the anatomical structure information of the examinee, in parallel with the second medical image; registering the second medical image and the first medical image to each other; changing the display of the second medical image in response to a user input for the second medical image; and changing the display of the first medical image in response to the changed display of the second medical image.

In accordance with still another aspect of the present invention, there is provided a computing system for identifying and visualizing a thrombosis, the computing system including: a receiving module configured to receive a first medical image of an examinee acquired by a medical image diagnostic apparatus; a database configured to store a computer tomography angiography (CTA) image-based average standard model; and a processor configured to receive the average standard model from the database, and to perform an image processing process on the first medical image received by the receiving module. In this case, the processor is further configured to register the first medical image and the CTA image-based average standard model to each other, and to identify a candidate blood vessel region from the first medical image based on results of the registration. The processor is further configured to acquire a volume, selected by applying a threshold value for the brightness of the first medical image to the candidate blood vessel region, as a first thrombosis candidate region, and to acquire at least part of the first thrombosis candidate region as a second thrombosis candidate region based on the size information of the first thrombosis candidate region. The processor is further configured to visualize the second thrombosis candidate region by assigning a visual effect, adapted to distinguish the second thrombosis candidate region from the remaining portion of the first medical image, to the second thrombosis candidate region.

In accordance with still another aspect of the present invention, there is provided a computing system for identifying and visualizing a thrombosis, the computing system including: a receiving module configured to receive a second medical image, i.e., a computer tomography angiography (CTA) image of an examinee acquired by a medical image diagnostic apparatus; a database configured to store a CTA image-based average standard model; and a processor configured to receive the average standard model from the database, and to perform an image processing process on the first medical image received by the receiving module. In this case, the processor is further configured to identify a blood vessel region from the first medical image, and to register the identified blood vessel region and the average standard model to each other. The processor is further configured to detect a thrombosis-occluded region based on a difference between the identified blood vessel region and the average standard model, and to visualize the detected thrombosis-occluded region by assigning a visual effect, adapted to distinguish the detected thrombosis-occluded region from the remaining portion of the second medical image, to the detected thrombosis-occluded region.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Preferred embodiments of the present invention will be described in detail below with reference to the accompanying drawings. In the following description of the present invention, when it is determined that a detailed description of a known element or function may unnecessarily make the gist of the present invention obscure, the detailed description will be omitted.

Figure 1:
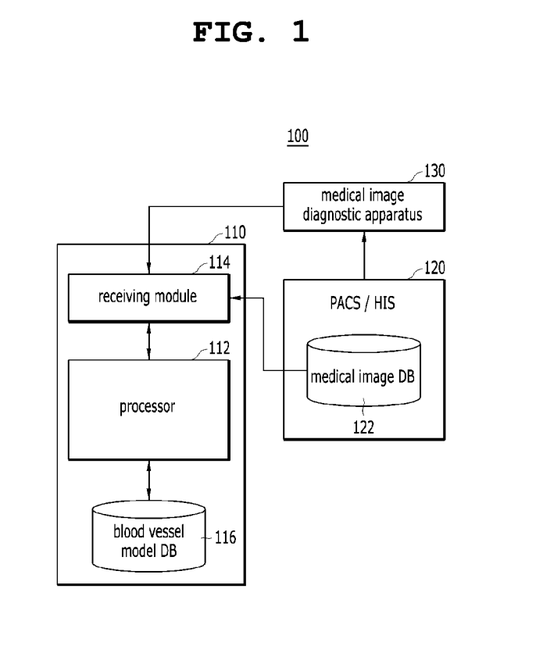
FIG. 1 is a block diagram showing a computing system for identifying and visualizing a cerebral thrombosis according to an embodiment of the present invention.

FIG. 1 is a block diagram showing a computing system 110 for identifying and visualizing a cerebral thrombosis according to an embodiment of the present invention.

Referring to FIG. 1, an overall high-hierarchy network system 100 including the computing system 110 includes a picture archiving and communication system/hospital information system (PACS/HIS) 120 and a medical image diagnostic apparatus 130, in addition to the computing system 110.

The PACS/HIS 120 includes a medical image DB 122. In other words, medical images acquired via the medical image diagnostic apparatus 130 may be stored in the medical image DB 122, and may be shared with individual computing terminals according to a diagnostic purpose.

The medical image diagnostic apparatus 130 refers to a CT scanner, an X-ray machine, an MRI scanner, and/or the like, and acquires a CT, CTA, MRI, and/or MRA image, and/or the like from an examinee.

The computing system 110 includes a processor 112, a receiving module 112, and a blood vessel model DB 116. The blood vessel model DB 116 refers to a kind of collection of data, i.e., a collection of data including all of data elements acquired via a pre-processing process, links between the data elements, information about the weights of respective links, etc. Blood vessel models stored in the blood vessel model DB 116 may provide average and standard organ models for cerebral blood vessels.

The blood vessel models may be average standard blood vessel images which are each acquired via a process of collecting, sampling, averaging and standardizing a plurality of CTA images. In other words, images of a plurality of patients are sampled. In this case, the blood vessel models may be collections of average values acquired in a standardized state through classification based on the personal information (ages, genders, medical histories, the types of diseases, etc.) of patients. In this case, individual pieces of raw data may be linked to each other based on common patient information, medical image diagnostic apparatus information, and/or the like, and average values may be acquired with weights assigned in accordance with the attributes of the links.

The receiving module 114 may receive a CT or CTA image of an examinee acquired via the medical image diagnostic apparatus 130. The receiving module 114 may receive a medical image directly from the medical image diagnostic apparatus 130, or may receive medical image data which has been stored in the medical image DB 122 after being acquired via the medical image diagnostic apparatus 130.

The processor 112 receives an average standard blood vessel model from the blood vessel model DB 116. The processor 112 may perform an image processing process on the CT or CTA image received by the receiving module 114.

In a first embodiment of the present invention, there is described a case where a non-contrast enhanced CT image is set as a main medical image. In this case, the processor 112 registers a first medical image (a CT image) and a CTA image-based average standard blood vessel model to each other, and identifies a candidate blood vessel region from the CT image based on the results of the registration. The candidate blood vessel region is acquired by excluding a region, where possibility that a blood vessel is present is extremely low, from the overall CT image based on the results of the registration. Since the following image processing process is performed within the candidate blood vessel region, a process of identifying a candidate blood vessel region has advantages of appropriately limiting the target range of an overall image processing process and reducing unnecessary computation. The processor 112 acquires a volume, selected by applying a threshold value for the brightness of the CT image to the candidate blood vessel region, as a first thrombosis candidate region. In this case, brightness values and the range thereof known as appearing in CT images due to thrombosis compositions may be represented using the Hounsfield scale. An upper limit/a lower limit known to be clinically significant as the brightness values of thrombosis compositions in a CT image may be used as a threshold value. The processor 112 excludes a portion of the first thrombosis candidate region inappropriate for the size of a thrombosis or blood vessel from the first thrombosis candidate region based on the size information of the first thrombosis candidate region. At least part of the first thrombosis candidate including the remaining region is acquired as a second thrombosis candidate region by the processor 112. In other words, the thrombosis candidate region is filtered by taking into consideration both the brightness values of the CT image and the size information of the identified region.

The processor 112 visualizes the second thrombosis candidate region by assigning a visual effect, adapted to distinguish the second thrombosis candidate region from the remaining portion of the CT image, to the second thrombosis candidate region. The second thrombosis candidate region may be displayed to be distinguished from the other region by the threshold value for the brightness value of the CT image based on the thrombosis composition. Accordingly, even when a separate visual effect is not assigned to the second thrombosis candidate region, the second thrombosis candidate region may be visualized to be distinguished from the remaining portion of the CT image. In this case, in order to prevent a region other than the thrombosis candidate region from causing confusion because the brightness values of the CT image are accidentally similar to each other, a region may be visualized only within a range set to the candidate blood vessel region.

The processor 112 may discriminate a first region (a region which appears for blood vessels to be distributed therein in the CTA image-based average standard model), where blood vessels are distributed, from the CT image of the examinee based on the results of the registration to the average standard model. The processor 112 may set at least part or all of the discriminated first region as a candidate blood vessel region.

In this case, since the diameters of the blood vessels of the standard model range from about 3 to 5 mm and thus this is excessively strict in the case of use for a candidate region in an image processing process, a process of performing dilation while maintaining shapes may be performed. The candidate blood vessel region within the CT image may be determined via a process of dilating the candidate blood vessel region by the processor 112.

The processor 112 may receive the CTA image (a second medical image) of the examinee via the receiving module 114 in addition to the CT image of the examinee.

In this case, it is assumed that the CT image and the CTA image are medical images acquired together for the same patient and are easy to register at least predetermined or larger ratio. The CT image and the CTA image may be cross-linked with each other through a synchronization/crosslink process so that a user input for any one of them can influence the display of the other image.

The processor 112 may display the CT image and the CTA image in parallel on a display. The processor 212 registers the CT image and the CTA image to each other. For example, when a user input is received on a window on which the CT image is being displayed and the display of the CT image is changed by the user input, the display of the cross-linked CTA image may be changed in response to the changed display of the CT image. In this case, the user input may be a user command, such as zoom-in/out, panning, rotation, parallel translation, or the like. A crosslink option may be used to, when an CT image and a CTA image are acquired together for the same patient, display the CT image and the CTA image in parallel on left and right window screens and compare the locations of the CT image and the CTA image with each other. If a disconnected portion of a blood vessel can be searched for in the CTA image of the same patient, higher registration performance can be achieved during a process of searching for a thrombosis candidate region in a CT image. In other words, the presence of a thrombosis can be predicted with higher accuracy during a process of searching for a thrombosis candidate region in the CT image by searching for a disconnected portion of a blood vessel in the CTA image.

The registration between the CT image and the CTA image is performed on a 3D volume. A rigid registration model and a non-rigid registration model may be selectively used. A registered candidate blood vessel region may be displayed in all CT or CTA slices.

A rigid registration model and a non-rigid registration model on a 3D volume may be used for the registration between a CT image and a CTA image, and may be also used for the registration between a CT image and an average standard blood vessel model and/or the registration between a CTA image and an average standard blood vessel model.

In the first embodiment, it is assumed that the CT image is a basic image and the CTA image auxiliary supports the analysis of the CT image. In this case, a thrombosis-occluded region where a disconnection or an omission in a blood vessel appears may be detected in the CTA image registered to the CT image. A region of the detected thrombosis-occluded region which matches the previously analyzed second thrombosis candidate region (a region acquired from the CT image) may be detected as a final thrombosis location region.

A second embodiment is an embodiment in which it is assumed that the CTA image of the examinee is a basic image (a second medical image). In this case, the processor 112 may identify a blood vessel region in the CTA image. Since the CTA image has contrast-enhanced blood vessel information, a process of identifying a blood vessel region may be relatively easily performed. The processor 112 registers the identified blood vessel region and a CTA image-based average standard blood vessel model to each other. In this case, a registration process presupposes a 3D volume. Rigid registration and non-rigid registration may be selectively used according to the situation, as described above.

The processor 112 may detect a thrombosis-occluded region based on a difference between the identified blood vessel region and the registered average standard blood vessel model. In other words, when at least a part of a contrast-enhanced blood vessel is not shown at a location, at which a blood vessel has to be present according to the average standard blood vessel model, in the CTA image of the examinee, it may be determined that possibility that a blood vessel is occluded is high, and the region in question may be detected as a thrombosis-occluded region.

The processor 112 may visualize the detected thrombosis-occluded region by assigning a visual effect, adapted to distinguish the detected thrombosis-occluded region from the remaining portion of the second medical image (the CTA image) of the examinee, to the detected thrombosis-occluded region.

In this case, the thrombosis-occluded region refers to a case where a branch of a cerebral blood vessel is occluded by a thrombosis. Although the occlusion of a blood vessel may be generated by other causes, a thrombosis may be first considered to be the cause of the occlusion in the case where a blood vessel itself is occluded to the extent that contrast-enhanced blood does not flow. Accordingly, in the case where part of a cerebral blood vessel through which blood has flowed is abruptly occluded and then blood does not flow, possibility that the cerebral blood vessel is occluded by a thrombosis may be taken into consideration.

In the second embodiment, when a CT image (a first medical image) can be acquired along with the CTA image (the second medical image), the processor 112 may register the CTA image and the CT image to each other, and may visualize the thrombosis-occluded region, detected from the CTA image, on an anatomical structure, included in the CT image, as a thrombosis candidate region. In this case, the location where the detected thrombosis-occluded region is displayed on the CT image may be acquired through the registration between the CT image and the CTA image.

Even in the second embodiment, when the CTA image and the CT image are acquired together and can be displayed in parallel, the processor 112 may perform control so that a user input for any one image can influence both the medical images (the CT image and the CTA image) in the same way and can change the visual representation of both the medical images through a crosslink option between the CT image and the CTA image.

In a third embodiment of the present invention, a process of generating an average standard blood vessel model based on a plurality of CTA image samples is described.

The processor 112 may receive a first sample image of a CTA image via the receiving module 114.

The processor 112 may segment a first cerebral blood vessel region from the first sample image. The processor 112 may set the first center line of the first cerebral blood vessel region, and may measure the first diameter of the first cerebral blood vessel region in the first sample image.

The processor 112 may generate a CTA image-based average standard model by using information about the first boundary of the first cerebral blood vessel region, information about the first center line of the first cerebral blood vessel region, and information about the first diameter of the first cerebral blood vessel region.

Meanwhile, the processor 112 may receive a second sample image of the CTA image, and may segment a second cerebral blood vessel region from the second sample image. The processor 112 may be set the second center line of the second cerebral blood vessel region, and may measure the second diameter of the second cerebral blood vessel region.

The processor 112 may update the CTA image-based average standard model based on information about the second boundary of the second cerebral blood vessel region, information about the second center line of the second cerebral blood vessel region, and information about the second diameter of the second cerebral blood vessel region.

In this case, the processor 112 may set a link between the first sample image and the second sample image, furthermore links between a plurality of sample images, by taking into consideration the personal information of the examinee, i.e., the subject of the CTA image, such as the age, gender, type of disease, seriousness of a disease, height, weight, etc. of the examinee, may set each item of the personal information as a parameter, may delimit and arrange related CTA sample images for each parameter, and may then generate and update an average standard blood vessel model in the delimited and arranged state.

Figure 2:
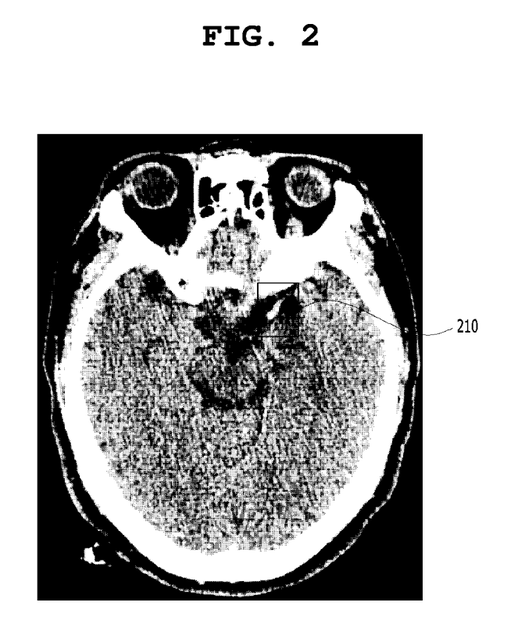
FIG. 2 is a view showing a process of searching for a cerebral thrombosis candidate region in a general CT image based on brightness values.

FIG. 2 is a view showing a process of searching for a cerebral thrombosis candidate region in a general CT image based on brightness values. At least part of FIG. 2 shows part of the process which is performed in the present invention, which is included in part of the configuration of the present invention.

When a threshold value within a range known as the brightness values of thrombosis compositions is applied to a general cerebral CT image, a region including an actual thrombosis will be brightened through processing. However, the composition of a thrombosis has a CT image brightness value similar to those of compositions of organs adjacent to a blood vessel particularly in the brain, a brightened candidate region (a candidate region corresponding to the threshold value) is activated throughout an overall image, as shown in FIG. 2. A region which has to be actually diagnosed as a thrombosis in the above brightened candidate region is only a region corresponding to a region 210, and thus the other region appearing throughout the overall cerebral image corresponds to organs which function normally.

According to the present invention, a thrombosis is searched for by performing visualization through the application of a threshold value for the brightness values of thrombosis compositions or the range of the brightness values to a cerebral CT image. However, in order to prevent a phenomenon in which organs other than a thrombosis are visualized throughout an overall range from occurring, the range of a region to be visualized is reduced using a CTA image-based average standard blood vessel model, thereby preventing confusion from being caused.

Figure 3:
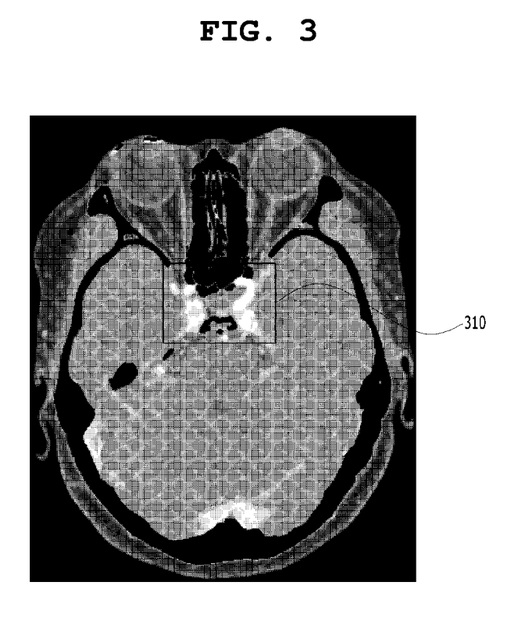
FIG. 3 is a sample image showing a contrast-enhanced cerebral blood vessel in a general CTA image.

FIG. 3 is a sample image showing a contrast-enhanced cerebral blood vessel in a general CTA image. At least part of FIG. 3 shows part of a process which is performed in the present invention, which is included in part of the configuration of the present invention.

Referring to FIG. 3, there is shown a region 310 in which a cerebral blood vessel is distinctively displayed by a contrast agent. The present invention intends to acquire a thrombosis candidate region with high accuracy by correlating a threshold value for the brightness values of the CT image shown in FIG. 2 or the range of the brightness values with the information of the contrast-enhanced cerebral blood vessel region shown in FIG. 3.

Figure 4:
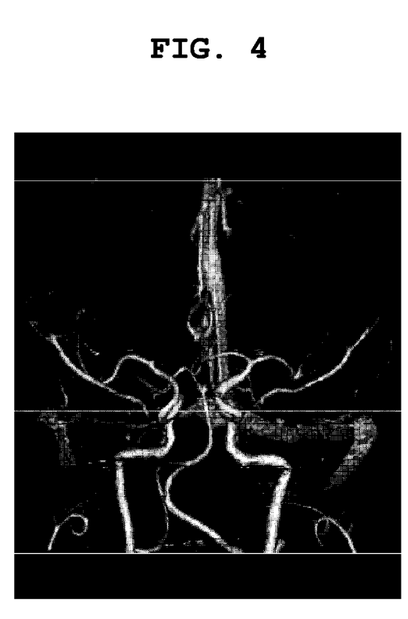
FIG. 4 is a view showing an example of an average standard blood vessel model acquired from a cerebral blood vessel CTA image according to an embodiment of the present invention.

FIG. 4 is a view showing an example of an average standard blood vessel model acquired from a cerebral blood vessel CTA image according to an embodiment of the present invention. FIG. 4 may be extracted from the shapes of a collection of data stored in the blood vessel model DB 116 of FIG. 1. An average standard model for cerebral blood vessels may be acquired by collecting and analyzing a plurality of CTA image samples. Meanwhile, the processor 112 may acquire an example of an examinee-customized average standard cerebral blood vessel model, such as that shown in FIG. 4, by collecting the data sets of at least part of the blood vessel models stored in the blood vessel model DB 116 through the consideration of the personal information of an examinee, i.e., an analysis target, such as the age, gender, type of disease, seriousness of a disease, height, weight, etc. of the examinee.

The standardized average model for cerebral blood vessels may be provided in a customized form according to the age and gender of an examinee. For example, when the age of an examinee is higher, an average model for cerebral blood vessels may have more corves. The cerebral blood vessels of an examinee with a cerebral disease and the cerebral blood vessels of a healthy examinee may differ from each other in thickness or distribution.

Figure 5:
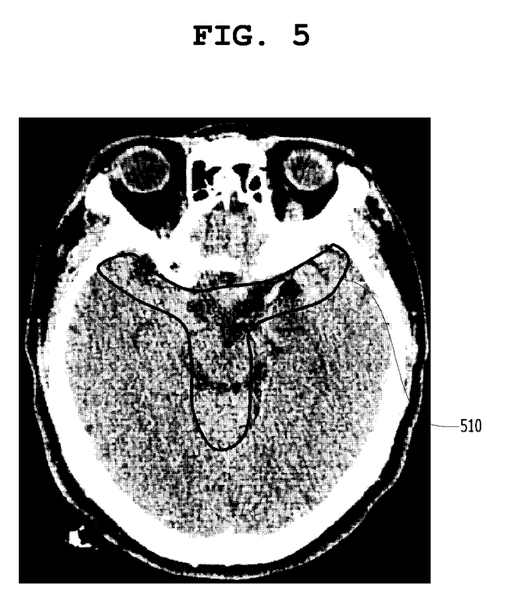
FIG. 5 is a view showing an example of an image in which a blood vessel model has been registered to a cerebral CT image according to an embodiment of the present invention.

FIG. 5 is a view showing an example of an image in which a blood vessel model has been registered to a cerebral CT image according to an embodiment of the present invention.

The CT image shown in FIG. 2 is registered to the blood vessel model of FIG. 4, and the portion of the CT image to which cerebral blood vessels have been registered is discriminated and displayed as a region 510 in FIG. 5.

Figure 6:
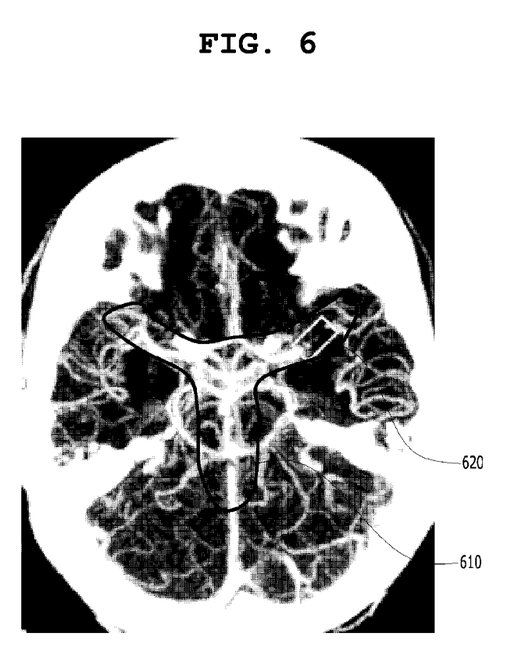
FIG. 6 is a view showing an example of an image in which a blood vessel model has been registered to a CTA cerebral blood vessel image according to an embodiment of the present invention.

FIG. 6 is a view showing an example of an image in which a blood vessel model has been registered to a CTA cerebral blood vessel image according to an embodiment of the present invention.

Referring to FIG. 6, a portion to which the standard blood vessel model has been registered appears as a first region 610. In the CTA image, a portion in which a blood vessel has been occluded and which is diagnosed as a thrombosis appears as a second region 620. In other words, when the occlusion of a blood vessel is detected within the first region 610, it may be considered to be a strong thrombosis candidate region.

Figure 7:
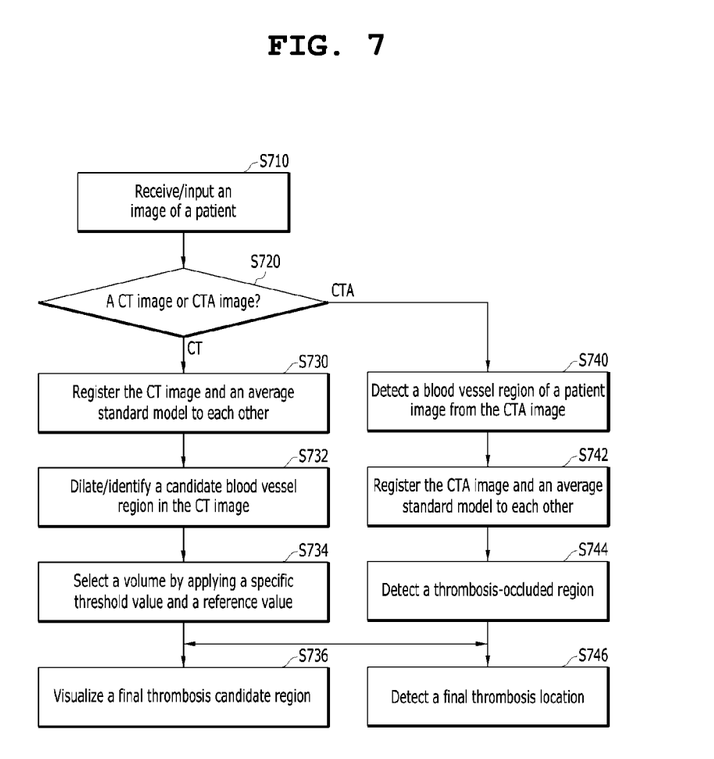
FIG. 7 is an operation flowchart showing a method of identify and visualizing a cerebral thrombosis according to an embodiment of the present invention.

FIG. 7 is an operation flowchart showing a method of identifying and visualizing a cerebral thrombosis according to an embodiment of the present invention.

The method of FIG. 7 may be performed by instruction program code loaded onto the processor 112 of the computing system 110 shown in FIG. 1, or the like. When the reception/input of an image of a patient via the receiving module 114 is detected by the processor 112 at step S710, the processor 112 determines whether the image of the patient is a CT image or CTA image at step S720.

When the image of the patient is a CT image, steps S730 to S736 are performed. In contrast, when the image of the patient is a CTA image, steps S740 to S746 are performed. When the CT and CTA images of the patient are simultaneously received/input, steps S730 to S736 and steps S740 to S746 are all performed. The results of the performance of the two processes may be shared after steps S734 and S744, and may be utilized to further increase the accuracy of the detection of a final thrombosis candidate region and a final thrombosis location.

At step S730, the CT image of the patient and an average standard blood vessel model are registered to each other by the processor 112. In this case, the average standard blood vessel model is acquired by analyzing a plurality of samples of the CTA image. At step S732, a candidate blood vessel region is dilated and identified in the CT image of the patient by using the results of the registration at step S730 by the processor 112. At step S734, a volume is selected within the candidate blood vessel region by applying a threshold value for a specific CT image and a reference value for a volume size by the processor 112. In this case, the selected volume is visualized as a thrombosis candidate region at step S736. In order to increase the accuracy of step S736, information about the CTA image-based thrombosis-occluded region detected at step S744 may be utilized.

At step S740, the blood vessel region of the patient image is detected from the CTA image of the patient by the processor 112. At step S742, the CTA image of the patient and the average standard blood vessel model are registered to each other by the processor 112. At step S744, when a blood vessel is not present at a location where the blood vessel must be present or when a blood vessel is disconnected or at least a part of the blood vessel is absent, a thrombosis-occluded region is detected based on the results of the registration at step S742 by the processor 112. At step S746, a final thrombosis location is detected in the CTA image through the image analysis of the detected thrombosis-occluded region. In this case, in order to increase the accuracy of the detection of step S746, information about the CT image-based thrombosis candidate region/volume selected at step S734 may be utilized, and information about the anatomical structures of the internal organs of the patient included in the CT image may be utilized.

Figure 8:
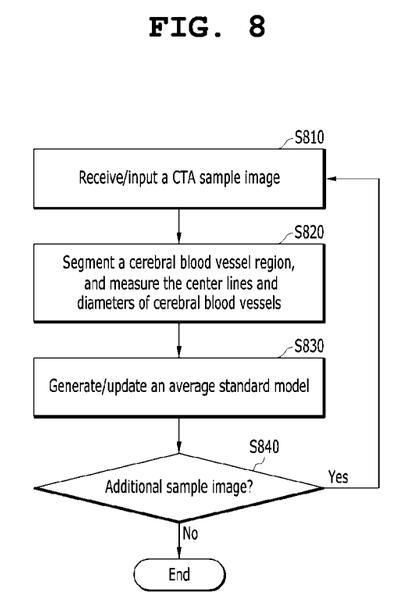
FIG. 8 is an operation flowchart showing a pre-processing process of generating a cerebral blood vessel average standard model for the identification and visualization of a cerebral thrombosis according to an embodiment of the present invention.

FIG. 8 is an operation flowchart showing a pre-processing process of generating a cerebral blood vessel average standard model for the identification and visualization of a cerebral thrombosis according to an embodiment of the present invention.

The process of FIG. 8 may be performed by the processor 112 of FIG. 1.

At step S810, the processor 112 receives a CTA sample image which is received via the receiving module 114. At S820, the processor 112 segments a cerebral blood vessel region from the CTA sample image, and measures the center lines and diameters of cerebral blood vessels. At S830, the processor 112 may generate and update an average standard model based on cerebral blood vessel region segmentation information, center line information, and diameter information regarding accumulated CTA sample images.

The processor 112 may update the average standard model and increase the completeness of the average standard model by repeating steps S810 to S830 until there is no additional sample image.

The method of identifying and visualizing a cerebral thrombosis according to the embodiment of the present invention may be implemented in the form of program instructions executable by a variety of computer means, and may be stored in a computer-readable storage medium. The computer-readable storage medium may include program instructions, a data file, and a data structure solely or in combination. The program instructions which are stored in the medium may be designed and constructed particularly for the present invention, or may be well known and available to those skilled in the field of computer software. Examples of the computer-readable storage medium include magnetic media such as a hard disk, a floppy disk and a magnetic tape, optical media such as CD-ROM and a DVD, magneto-optical media such as a floptical disk, and hardware devices particularly configured to store and execute program instructions such as ROM, RAM, and flash memory. Examples of the program instructions include not only machine language code that is constructed by a compiler but also high-level language code that can be executed by a computer using an interpreter or the like. The above-described hardware components may be configured to act as one or more software modules that perform the operation of the present invention, and vice versa.

According to the present invention, a candidate region where there is possibility that a thrombosis is present can be selected even from a general CT image. Furthermore, according to the present invention, a target region in which a thrombosis is searched for can be reduced, and thus an examiner can easily and accurately search for and analyze a thrombosis.

According to the present invention, there can be resolved a problem in which it is difficult to search for a thrombosis because a contrast between a thrombosis and adjacent tissues is not obvious in a CT image. According to the present invention, a thrombosis can be accurately searched for by using a specific threshold value (ranging from 40 to 100 HU) for a thrombosis and rapidly excluding a region, other than a cerebral blood vessel, from a search target range.

According to the present invention, the accuracy of a search for a thrombosis can be increased in selective conjunction with a contrast-enhanced CTA image. According to the present invention, an average standard model can be generated by segmenting only important cerebral blood vessel regions from a plurality of CTA images. According to the present invention, there can be provided an average standard model which can function as a mask layer required for the selection of a candidate region where there is possibility that an actual blood vessel is present, and a method of utilizing the average standard model.

According to the present invention, when both CT and CTA images of the same patient are simultaneously utilized, the accuracy of a search for a thrombosis can be further increased.

However, the present invention is limited and restricted by the embodiments. Throughout the drawings, the same reference symbols denote the same members. The lengths, heights, sizes, widths, etc. introduced in the embodiments and drawings of the present invention may be exaggerated to help an understanding of the present invention.

While the present invention has been described in conjunction with specific details, such as specific components, and limited embodiments and diagrams above, these are provided merely to help an overall understanding of the present invention. The present invention is not limited to these embodiments, and various modifications and alterations may be made based on the foregoing description by those having ordinary knowledge in the art to which the present invention pertains.

Therefore, the technical spirit of the present invention should not be determined based only on the described embodiments, and not only the following claims but also all equivalents to the claims and equivalent modifications should be construed as falling within the scope of the spirit of the present invention.

What is claimed is:

1. A method of identifying and visualizing a thrombosis, the method comprising:
   registering an acquired computer tomography (CT) image of an examinee and a computer tomography angiography (CTA) image-based average standard model to each other;
   identifying a candidate blood vessel region from the CT image of the examinee based on results of the registration to the average standard model;
   acquiring a volume, selected by applying a threshold value for brightness of the CT image to the candidate blood vessel region, as a first thrombosis candidate region;
   acquiring at least part of the first thrombosis candidate region as a second thrombosis candidate region based on size information of the first thrombosis candidate region; and
   visualizing the second thrombosis candidate region by assigning a visual effect, adapted to distinguish the second thrombosis candidate region from a remaining portion of the CT image of the examinee, to the second thrombosis candidate region.

2. The method of claim 1, wherein the identifying comprises:
   discriminating a first region where blood vessels are distributed from the CT image of the examinee based on the results of the registration to the average standard model; and
   setting at least part of the discriminated first region as the candidate blood vessel region.

3. The method of claim 1, further comprising:
   displaying an acquired computer tomography angiography (CTA) image of the examinee, in parallel with the CT image;
   registering the CTA image and the CT image to each other;
   changing the display of the CT image in response to an user input for the CT image; and
   changing the display of the CTA image in response to the changed display of the CT image.

4. The method of claim 3, further comprising:
   detecting a thrombosis-occluded region where a blood vessel is disconnected or at least a part of the blood vessel is absent in the CTA image registered to the CT image; and
   detecting a region of the detected thrombosis-occluded region matching the second thrombosis candidate region as a thrombosis location region.

5. The method of claim 1, further comprising:
   receiving a first sample image including a CTA image;
   segmenting a first cerebral blood vessel region from the first sample image;
   setting a first center line of the segmented first cerebral blood vessel region, and measuring a first diameter of the first cerebral blood vessel region; and
   generating the CTA image-based average standard model by using information about a first boundary of the segmented first cerebral blood vessel region, information about the first center line of the first cerebral blood vessel region, and information about the first diameter of the first cerebral blood vessel region.

6. The method of claim 5, further comprising:
   receiving a second sample image including another CTA image;
   segmenting a second cerebral blood vessel region from the second sample image;
   setting a second center line of the segmented second cerebral blood vessel region, and measuring a second diameter of the second cerebral blood vessel region; and
   updating the CTA image-based average standard model based on information about a second boundary of the segmented second cerebral blood vessel region, information about the second center line of the second cerebral blood vessel region, and information about the second diameter of the second cerebral blood vessel region.

7. A method of identifying and visualizing a thrombosis, the method comprising:
   identifying a blood vessel region from an acquired computer tomography angiography (CTA) image of an examinee;
   registering the identified blood vessel region and a CTA image-based average standard model to each other;
   detecting a thrombosis-occluded region based on a difference between the identified blood vessel region and the registered average standard model; and
   visualizing the detected thrombosis-occluded region by assigning a visual effect, adapted to distinguish the detected thrombosis-occluded region from a remaining portion of the CTA image of the examinee, to the detected thrombosis-occluded region.

8. The method of claim 7, wherein the detecting comprises identifying a region of the identified blood vessel region, where a blood vessel is disconnected or at least a part of the blood vessel is absent, as the thrombosis-occluded region by comparing the identified blood vessel region with the average standard model.

9. The method of claim 7, further comprising:
   receiving a computer tomography (CT) image including anatomical structure information of the examinee;
   registering the CTA image and the CT image to each other; and
   visualizing the thrombosis-occluded region, detected from the CTA image, in the CT image registered to the CTA image.

10. The method of claim 7, further comprising:
    displaying a computer tomography (CT) image, including anatomical structure information of the examinee, in parallel with the CTA image;
    registering the CT image and the CTA image to each other;
    changing the display of the CTA image in response to a user input for the CTA image; and
    changing the display of the CT image in response to the changed display of the CTA image.

11. A computing system for identifying and visualizing a thrombosis, the computing system comprising:

a receiving module configured to receive a computer tomography (CT) image of an examinee acquired by a medical image diagnostic apparatus;

a database configured to store a computer tomography angiography (CTA) image-based average standard model; and a processor configured to:
receive the average standard model from the database;
register the CT image and the CTA image-based average standard model to each other, and identify a candidate blood vessel region from the CT image based on results of the registration;
acquire a volume, selected by applying a threshold value for brightness of the CT image to the candidate blood vessel region, as a first thrombosis candidate region, and acquire at least part of the first thrombosis candidate region as a second thrombosis candidate region based on size information of the first thrombosis candidate region; and
visualize the second thrombosis candidate region by assigning a visual effect, adapted to distinguish the second thrombosis candidate region from a remaining portion of the CT image, to the second thrombosis candidate region.

12. The computing system of claim 11, wherein the processor is further configured to:
discriminate a first region where blood vessels are distributed from the CT image based on results of the registration to the average standard model; and
set at least part of the first region as the candidate blood vessel region.

13. The computing system of claim 11, wherein:
the receiving module is further configured to receive a computer tomography angiography (CTA) image of the examinee; and
the processor is further configured to:
register the CTA image and the CT image to each other, and display the CTA image on a display in parallel with the CT image; and
change the display of the CT image in response to a user input for the CT image, and change the display of the CTA image in response to the changed display of the CT image.

14. A computing system for identifying and visualizing a thrombosis, the computing system comprising:
a receiving module configured to receive a computer tomography angiography (CTA) image of an examinee acquired by a medical image diagnostic apparatus;
a database configured to store a CTA image-based average standard model; and
a processor configured to:
receive the average standard model from the database;
identify a blood vessel region from the CTA image, and register the identified blood vessel region and the average standard model to each other; and
detect a thrombosis-occluded region based on a difference between the identified blood vessel region and the average standard model, and visualize the detected thrombosis-occluded region by assigning a visual effect, adapted to distinguish the detected thrombosis-occluded region from a remaining portion of the CTA image, to the detected thrombosis-occluded region.

15. The computing system of claim 14, wherein the processor is further configured to identify a region of the identified blood vessel region, where a blood vessel is disconnected or at least a part of the blood vessel is absent, as the thrombosis-occluded region by comparing the identified blood vessel region with the average standard model.

16. The computing system of claim 14, wherein:
the receiving module is further configured to receive a computer tomography (CT) image including anatomical structure information of the examinee; and
the processor is further configured to:
register the CTA image and the CT image to each other; and
visualize the thrombosis-occluded region, detected from the CTA image, in the CT image registered to the CTA image.

\* \* \* \* \*